United States Patent [19]
Moldt

[11] Patent Number: 5,990,312
[45] Date of Patent: Nov. 23, 1999

[54] METHOD FOR THE PREPARATION OF ESTERS OF ANHYDROECGONINE

[75] Inventor: Peter Moldt, Humlebaek, Denmark

[73] Assignee: Neurosearch A/S, Glostrup, Denmark

[21] Appl. No.: 08/913,446

[22] PCT Filed: Mar. 22, 1996

[86] PCT No.: PCT/EP96/01277

§ 371 Date: Nov. 4, 1997

§ 102(e) Date: Nov. 4, 1997

[87] PCT Pub. No.: WO96/30371

PCT Pub. Date: Oct. 3, 1996

[30] Foreign Application Priority Data

Mar. 24, 1995 [DK] Denmark ................. 0302/95

[51] Int. Cl.⁶ .............. C07D 451/02; C07D 451/10
[52] U.S. Cl. ............................ 546/132; 546/127
[58] Field of Search ................................ 546/132

[56] References Cited

U.S. PATENT DOCUMENTS 5,506,359 4/1996 Madras et al. .................. 546/130

FOREIGN PATENT DOCUMENTS 0604355 6/1994 European Pat. Off. .

OTHER PUBLICATIONS

L.G.Wadw,jr. Organic Chemistry, p. 349, Prentice Hall publishers, 1987.
Majewski, M. and Zheng, G., "Stereoselective deprotonation of tropinone and reactions of tropinone lithium enolate", Canadian Journal of Chemistry, vol. 70, pp. 2618–2626 (1992).

*Primary Examiner*—Alan L. Rotman
*Attorney, Agent, or Firm*—Birch, Stewart, Kolasch & Birch, LLP

[57] ABSTRACT

The present invention discloses compounds of the formula

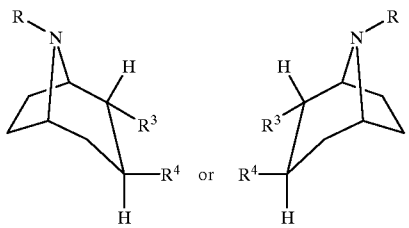

any mixture thereof, or a pharmaceutically acceptable salt thereof;

wherein R, $R^3$, and $R^4$ each have the meanings set forth in the specification.

The compounds possess valuable pharmaceutical properties as dopamine reuptake inhibitors.

5 Claims, No Drawings

METHOD FOR THE PREPARATION OF ESTERS OF ANHYDROECGONINE

CROSS-REFERENCE

This application is a 371 of PCT/U.S. 96/01277 filed Mar. 22, 1996.

The present invention relates to a novel process for the preparation of esters of anhydroecgonine from cocaine and derivatives thereof. Esters of anhydroecgonine are useful intermediates in the preparation of pharmaceutically active tropane derivatives.

BACKGROUND OF THE INVENTION AND PRIOR ART

Several publications describe conversions of cocaine to anhydroecgonine where the conversion is effected by heating cocaine in aqueous acid (hydrochloric or sulphuric acid) or with benzoic acid for several hours (de Jong, Recl. Trav. Chim. Pays-Bas, 56 (1937), pages 187–201 and Chem. Ber., 21 (1888), pages 3029–3045). At the time of the references cited above, the analytical methods available for the qualitative and quantitative determination of chemical compounds were limited, which makes the results obtained highly uncertain. Furthermore there is a lack of precise descriptions of how the reactions were carried out.

Several attempts to convert ecgonine or cocaine to anhydroecgonine in alkaline solutions or by heating in water, giving poor results, have also been described. In fact it seems that alkaline solutions favour isomerisation (de Jong, Recl. Trav. Chim. Pays-Bas, 56 (1937), pages 192–194.

In later references Anhydroecgonine and esters thereof have been prepared by hydrolysis of cocaine in aqueous hydrochloric acid followed by dehydration with phosphorus oxychloride (J. Amer. Chem. Soc., 82 (1960), page 4643 and EP-A1-604 355 ). Although both the hydrolysis of cocaine and the dehydration of ecgonine produces high yields, it is a serious drawback to this method that the reaction mixture becomes syrupy during the dehydration step which makes stirring almost impossible. Using $SOCl_2$ as dehydrating agent causes similar problems.

Neither of these methods are thus suitable for large-scale production.

It has now surprisingly been found that esters of anhydroecgonine can be prepared in large-scale from cocaine or derivatives thereof using a convenient, high-yielding, one-pot synthesis.

The esters prepared according to the invention are useful intermediates in the preparation of pharmaceutically active tropane derivatives, see EP-A1-604 355).

OBJECTS OF THE INVENTION

It is an object of the invention to provide a novel method for preparing carboesters of anhydroecgonine, which is convenient, high-yielding and suitable for large-scale productions. Additional objects will be obvious to a person skilled in the art.

SUMMARY OF THE INVENTION

The invention then, inter alia comprises the following:

A process for the preparation of esters of anhydroecgonine having the formula

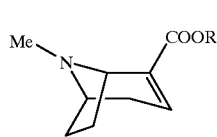

(I)

any of its enantiomers or any mixture thereof, or a salt thereof, wherein

R is alkyl, or optionally substituted aryl, or arylalkyl; comprising the step of reacting a compound of formula

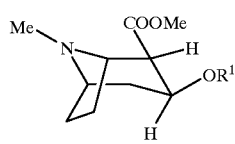

(II)

any of its enantiomers or any mixture thereof, or a salt thereof, wherein $R^1$ is hydrogen, alkyl-CO—, or optionally substituted aryl-CO—, or arylalkyl-CO—; with an alcoholate $RO^-$, $M^+$ wherein R is as defined above and $M^+$ is a counter ion, followed by isolation of the resulting compound either as the base or, if desired, in the form of a salt thereof;

such a process wherein the alcoholate is an alkalimetal alcoholate;

and such a process wherein the alkalimetal alcoholate is sodium ethanolate, potassium ethanolate, lithium ethanolate, sodium methanolate, potassium methanolate, or lithium methanolate.

In the above definition of R and $R^1$, alkyl means a straight-chained or branched chain of from one to six carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Aryl means an aromatic group, such as for example phenyl or napthyl which may substituted one or more times with alkyl, alkoxy, halogen, amino, nitro, cyano and trifluoromethyl for example.

Examples of salts of the compounds of formula (I) and (II) are acid addition salts including inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, may be useful in the preparation of salts useful as intermediates in obtaining compounds of the invention and their pharmaceutically acceptable acid addition salts.

It will be appreciated by those skilled in the art that the compounds having the formula (I) and (II) contain several chiral centres and that such compounds exist in the form of isomers (i.e. enantiomers). The invention includes all such enantiomers and any mixtures thereof including racemic mixtures.

Racemic mixtures can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. Racemic mixtures can thus be resolved into their optical antipodes, e.g. by fractional crystallization of d- or l-(tartrates, mandelates, or camphorsulphonate) salts for example. Racemic mixtures may also be resolved by the formation of diastereomeric amides by reaction of the compounds with an optically active activated carboxylic acid, such as that derived from (+) or (−) phenylalanine, (+) or (−) phenylglycine, (+) or (−) camphanic acid, or by the formation of diastereomeric carbamates by reaction with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

DETAILED DESCRIPTION OF THE INVENTION

The following scheme illustrates the process of the invention

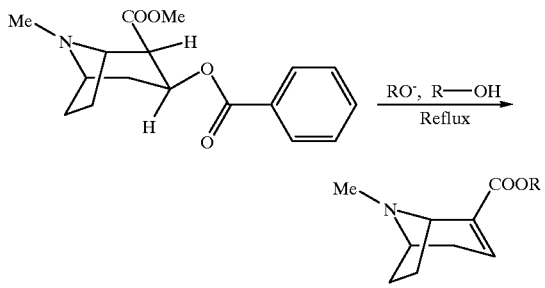

The process of the invention is suitably effected by heating the reaction components in an anhydrous organic solvent. Suitable organic solvents are for example an alcohol, such as methanol, ethanol, isopropanol or phenol, ethers such as diisopropylether, tetrahydrofuran or dioxan, amides such as dimethylformamide, esters such as ethylacetat or halogenated-, aromatic- or aliphatic hydrocarbons such as chloroform, dichlormethan, benzene, toluene, xylene and hexane.

The reaction temperature depends on the solvent used.

The obtained anhydroecgonine ester can be isolated using conventional methods, such as extraction, distillation, crystallisation, chromatography etc.

Starting materials are commercially available or can be prepared from commercially available materials using conventional methods.

EXAMPLES

The invention will now be described in greater detail with reference to the following example, which is given by way of illustration only and are not to be construed as limiting.

Anhydroecgonine Ethyl Ester

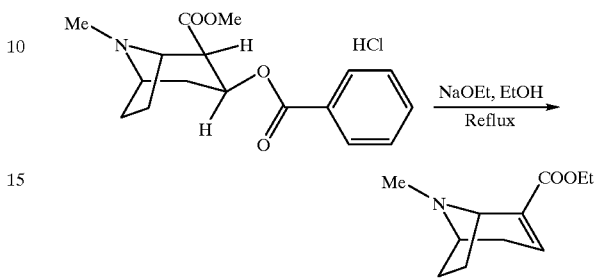

A solution of sodium ethanolate in ethanol was made by addition of sodium (103 g, 4.5 mol) to absolute ethanol (3.25 l) stirred at reflux temperature. When all sodium was reacted, the mixture was cooled to 70° C. and ethyl acetate (3 l) was added followed by cocaine hydrochloride (500 g, 1.47 mol)(optical active from natural sources, available from Belgopia). This mixture was stirred at reflux temperature under a nitrogen atmosphere for 2.5 hour, followed by slow addition of glacial acetic acid (150 ml, pH=7–8) to the warm mixture. Dry toluene (1.5 l) was added and an azeotrope of ethanol, ethyl acetate and toluene (temperature 30° C.) was distilled in vacuo (approximately 20 mbar). When approximately 2 l azeotrope has been collected, more toluene (2 l) was added and another portion (2 l) of azeotrope was distilled. This was repeated once more resulting in a total addition of 5.5 l toluene and distillation of approximately 6 l azeotrope. The resulting suspension of sodium chloride and sodium acetate in organic solvent was filtered and the filtrate was washed twice with toluene. The combined organic phases were concentrated in vacuo resulting in a yellow to brown oil. This oil was distilled at 15 mbar using a short vigreaux column, and ethyl benzoate was collected at 72–115° C., the vigreaux column was removed and the remanence was distilled at 0.2–0.5 mbar, and the title compound was collected at 67–78° C. as a clear slightly yellow oil. Yield 219.5 g=77%.

I claim:
1. A process for the preparation of esters of anhydroecgonine having the formula

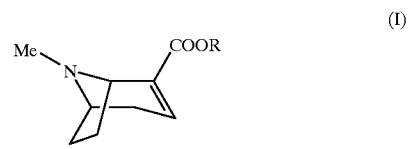

(I)

or a pharmaceutically acceptable acid addition salt thereof, wherein

R is alkyl, or optionally substituted aryl, or arylalkyl; comprising the step of reacting a compound of formula

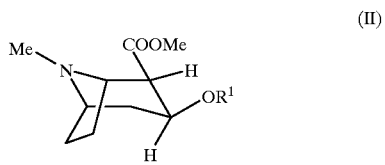

(II)

or a pharmaceutically acceptable acid addition salt thereof, wherein $R^1$ is hydrogen, alkyl-CO—, or optionally substituted aryl-CO—, or arylalkyl-CO—;

with an alcoholate $RO^-$, $M^+$ wherein R is as defined above and $M^+$ is a counter ion, followed by isolation of the resulting compound either as the base or, if desired, in the form of a pharmaceutically acceptable acid addition salt thereof.

2. A process as in claim 1 wherein the alcoholate is an alkalimetal alcoholate.

3. A process as in claim 2 wherein the alkalimetal alcoholate is sodium ethanolate, potassium ethanolate, lithium ethanolate, sodium methanolate, potassium methanolate, or lithium methanolate.

4. A process for the preparation of enantiomers of esters anhydroecgonine having the following formula

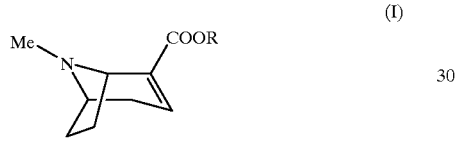

(I)

wherein R is alkyl, or optionally substituted aryl, or arylalkyl comprising the step of reacting an enantiomer of a compound of formula

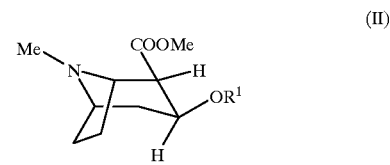

(II)

wherein $R^1$ is hydrogen, alkyl-CO—, or optionally substituted aryl-CO—, or arylalkyl-CO—;

with an alcoholate $RO^-$, $M^+$ wherein R is a s defined above and $M^+$ is a counter ion, followed by isolation of the resulting enantiomer.

5. The process of claim 1, wherein the anhydroecgonine of formula (I) is

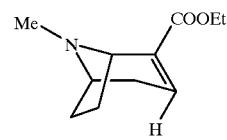

and the compound of formula (II) is

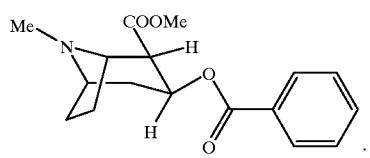

.

* * * * *